United States Patent [19]
Babian

[11] Patent Number: 5,632,774
[45] Date of Patent: May 27, 1997

[54] IN-THE-SHELL HYDRATION TO MAKE IMPLANT FILLER MATERIAL AND PROSTHESIS EMPLOYING SAME

[76] Inventor: Hamik Babian, 16820 Tribune St., Granada Hills, Calif. 91344

[21] Appl. No.: 645,749

[22] Filed: May 14, 1996

Related U.S. Application Data

[63] Continuation-in-part of Ser. No. 373,110, Jan. 17, 1995, abandoned.

[51] Int. Cl.⁶ .................................................. A61F 2/12
[52] U.S. Cl. ..................... 623/8; 623/11; 623/17; 623/66
[58] Field of Search ............... 623/11, 8, 7, 66, 623/17; 606/61

[56] References Cited

U.S. PATENT DOCUMENTS

| | | | |
|---|---|---|---|
| 4,138,382 | 2/1979 | Polmanteer | 260/29.6 |
| 4,138,383 | 2/1979 | Rembaum et al. | 260/29.7 |
| 5,116,371 | 5/1992 | Christensen et al. | 623/11 |
| 5,116,387 | 5/1992 | Berg | 623/66 |
| 5,192,326 | 3/1993 | Bao et al. | 623/17 |
| 5,219,360 | 6/1993 | Georgiade | 623/8 |
| 5,344,452 | 9/1994 | Lemperle | 623/11 |
| 5,407,445 | 4/1995 | Tautvydas et al. | 623/8 |
| 5,447,535 | 9/1995 | Muller . | |

OTHER PUBLICATIONS

Fredric L. Buchholz "Recent Advances in Superabsorbents"; TRIP vol. 2, No. 8, Aug., 277 (1994).

Arthur P. Worseg et. al. "Long Term Results of Inflatable Mammary Implants" British J. of Plasti Surg. (1995), 48, 183–188.

*Primary Examiner*—David Isabella

[57] ABSTRACT

A non-bleeding surgical breast implant containing mechanically stable 3-dimensional crosslinked hydrogel filler material hydrated directly inside a shell. Discrete polymeric hydrogel units at their smallest dehydrated solid dry state are placed into inconsiderable volume of a completely deflated shell through a sealable hole and subsequently are hydrated to a desired size either prior to or following implantation into a non-bleeding breast implant.

12 Claims, No Drawings

IN-THE-SHELL HYDRATION TO MAKE IMPLANT FILLER MATERIAL AND PROSTHESIS EMPLOYING SAME

CROSS-REFERENCE TO RELATED APPLICATIONS

This is a continuation-in-part patent application of U.S. patent application Ser. No. 08/373,110, filed on Jan. 17, 1995 now abandoned.

BACKGROUND OF THE INVENTION

1. Field of the Invention

The present invention relates to surgically implanted mammary expansive devices containing a biocompatable filler material inside a shell used for augmentation or reconstruction of breast tissue.

2. Description of the Related Art

Mammary prosthetic surgical implants are used to expand or to modify the volume or appearance of tissue in the area of the female breast.

Breast implants in current use consist of a flexible silicone rubber envelope or sack filled with salt and water solution called saline. In the past, implants filled with sticky silicone gel were commonly used in U.S., but the government restricted their use after there was concern about possible health problems attributed to silicone gel leaking from implants.

The saline-filled mammary implants commercially available in the U.S. are generally made by injecting saline into the shell through a port either at manufacturing plant site for fixed volume and predetermined size implants (non-inflatable) or in the operating room to the desired and adjustable sizes using serial progressive expanding injection technique, over the course of three to six months, while the implant is in the patient and everything is sewn closed (inflatable). The mammary tissue expanding surgical implant is used for restoring, improving, augmenting and reconstructing the female breast where the implant is placed under the breast tissue between the breast tissue and chest muscle or under the muscle itself.

The major problem that presents itself in the use of mammary prosthetic implants is that over time, the filler material tends to bleed and leak out of the shell causing deflation. For saline breast implant the leak is sudden and requires immediate implant removal or replacement.

Saline is considered harmless but of course, a leaky saline breast implant will need to be replaced by a new surgical operation since it will flatten like a deflated balloon.

Between Jan. 1, 1985, and Mar. 16, 1995, FDA received 19,296 adverse reports, including deflation, associated with saline breast implants. Furthermore, in 1995, Arthur P. Worseg, MD and co-workers published the study on 167 saline implants in 77 patients where the complete deflation was 22% from 1972 to 1984 and 26% from 1985 to 1992.

In addition to the major drawback of bleeding, published reports and studies are implicating the saline breast implants with other problems such as, wrinkling, folding, ridging, being less fleshy, not having shape memory and quick displacement of the saline solution and air present in the implant can create an audible sound or "slosh".

To overcome the saline drawbacks of wrinkling, folding, being less fleshy, having no holding power, and in general to improve overall acceptability of a saline-filled breast implant, researchers have focused attention on increasing saline consistency by mixing various kinds of polymeric water thickening or gelling agents with saline.

For example, U.S. Pat. No 4,138,382, to Polmanteer discloses a crosslinked water swellable or soluble gel as filling material for breast implant prosthesis. He also suggests placing insufficient amount of gel inside the shell where such a prosthesis can be implanted through a relatively small incision. Later-on after insertion, water can be added to increase the implant volume through swelling of gel filler material. Further, U.S. Pat. No 5,116,371, to Christensen, et al discloses a mammary prosthesis comprising a silicone outer container filled with hydrogel particles.

Thus, while providing clear advantages over simply implanting saline, all these new filler materials, with low or no crosslinking, are more or less soluble and are not able to retain or hold all the water within their loose polymeric structure resulting a blend of swollen and dissolved gel in free water. In this case, beside the possible seepage and transudation of loose gel or linear polymer through the shell, the free moving water is able to bleed out through the shell making a decrease in implant volume unavoidable after some time, requiring a new surgical operation to remove or replace deflated breast implant.

Thus, there is a great need to eliminate the problem of bleeding or leakage from mammary prosthesis, regardless of filler material considered to be harmless like saline or questionable like silicone gel, since a leaky implant needs to be replaced by a new surgical operation.

Accordingly, it would be a significant contribution to the medical device art to eliminate the major problem of bleeding or leakage and transudation from mammary prosthetic surgical implant by providing a non-bleeding harmless filler material capable of being used with existing mammary device manufacturing and breast surgical procedures practiced in the U.S. or elsewhere.

SUMMARY OF THE INVENTION

This invention relates to improved surgically implantable mammary tissue expanding prosthesis comprising an elastomeric shell that serves as a hollow soft container for discrete biocompatable hydrophilic crosslinked polymeric bodies or units as a new filler material. In more detail, the inventive new filler material is made from polymeric hydrogel macro unit or units at their smaller dehydrated state which are placed into the open shell to occupy a very small fraction of the total shell volume before sealing the implant. Later on, as it is required, water will swell hydrogel into the shape of the full sized shell as the hydrogel is hydrated by injecting sterile water into deflated shell either at manufacturing site or in operating room after breast implant is inserted in the patient. These hydrated hydrogel units are non-bleeding while conforming to the shape of the shell by assuming different viscoelastic packing arrangements as shell deforms in different positions when breast implant receiver moves in different direction.

According to this invention there is provided a method of preparing a new filler material used inside soft implantable mammary prosthesis which comprises placing into shell discrete dehydrated polymeric hydrogel bodies or units which swell in the shell to a larger soft hydrated units, where shell acts as a hydration flask or container. The dry units undergo physical change due to hydration inside the sealed shell into a non-pourable, non-bleedable resilient arrangement of so many soft gel-like units, conforming to the shape of the full sized shell.

Hydrogels are water-swellable polymer networks, and there is no precise and limiting definition of the term hydrogel units but for our purpose hydrogel units are mechanically stable, non-water-soluble, having a network of hydrophilic pores capable of trapping, retaining all implant injected water and expanding with water absorption, and can be either crosslinked or uncrosslinked, coated or non-coated, natural or synthetic and mono or polydispersed biocompatable units that swell on contact with water but do not dissolve. Hydrogel units are sometimes called superabsorbent polymers, and hydrogels in general are being extensively used and investigated as materials for different prosthetic devices, personal care products, food packaging, pharmaceuticals, wound dressing and sport medicine.

In a preferred embodiment, the hydrogel units are crosslinked polymers and are shaped as balls and beads capable of incorporating water into the polymeric matrix without dissolving in water.

It is yet another object of the invention to provide a filler material of very large water swollen polymeric macro unit or units with no free water in-between, capable of eliminating loss of either polymer or water from implant shell where the hydrogel unit is biodegradable or biostable capable of being easily cleared from the body through the normal urinary pathway if the breast implant were to rupture due to a traumatic injury.

It is therefore the main object of the present invention to provide a non-bleeding mammary prosthetic surgical implant that can be easily used with existing device manufacturing and surgical procedures practiced today where it is expected the implant to duplicate a feel as close as natural breast tissue.

The above and other aspects, features and advantages of the invention will become more fully apparent from the following disclosure, taken in conjunction with the appended claims.

DETAILED DESCRIPTION OF THE INVENTION

The present invention is based upon the discovery that the filler material required to occupy mammary prosthetic shell can be prepared directly inside the shell by hydration process of dehydrated hydrogel macro unit or units, capable of swelling to larger dimensions, placed inside the shell before the implant is sealed.

The present invention provides a breast tissue expanding prosthesis comprising: (a) a flexible hollow elastic shell or envelope container. (b) a method of placing discrete biocompatable crosslinked polymeric hydrogel bodies or units at their smallest dehydrated free flowing solid dry state inside the shell before sealing the implant. (c) injecting sterile water into the shell either before or after the mammary prosthesis has been implanted.

To have acceptable mechanical and behavioral characteristics of the implant, the consistency of the filler-material should be comparable to the softness of breast tissue to be replaced or augmented.

Accordingly, adjusting the consistency of individual filler forming hydrated hydrogel unit to a desired degree of softness can be easily done and is known in the art. For example, those skilled in the art will appreciate that the softness and elasticity of a hydrogel unit will depend on the degree of water swelling which in turn depends on the type of monomer, cross-linker, cross-linking density and further on the type of coating if the hydrogel unit is coated. Generally speaking, increasing hydrophilic functional groups like hydroxyl, amide, ethylene oxide and increasing the length of the polyfunctional hydrophilic soft segmented cross-linker used to make unit or the coating on the units, increases the water content of the hydrated hydrogel unit.

The shell or envelope may be formed of a physiological inert material which include several elastomers. The shell can be made from any suitable biocompatible material such as smooth or textured silicone, polyurethane, acrylates or others. For example, a completely cured cross-linked silicone rubber is preferred because of its strength and biocompatability. Such silicone shell or envelope can be made in accordance with the usual multiple dipping method employed commercially by manufacturers of conventional silicone breast prostheses as disclosed in U.S. Pat. Nos. 4,472,226; 4,455,691; and 4,955,909 or commercially available silicone shells made by Mentor Corp. (Santa Barbara, Calif.), Inamed Corp. (Las Vegas, Nev.), Nagor Limited (Isle of Man) and others may be used.

A completely deflated shell filled in only very small volume with free flowing solid dry hydrogel macro unit or units for use in the invention, capable of deforming by as many foldings as required into a reduced dimensions, may be surgically introduced in any known manner, through an incision into the patient where said incision having dimension much less than final dimension of implant at its maximum inflated state where at next stage water is introduced into the shell to increase swell volume and dimensions to the desired final size by hydration process.

Alternatively, prior to surgical insertion, fixed volume and pre-sized completely hydrated hydrogel filled breast implant can be prepared by the device manufacturer. The implant may then be surgically implanted through various well known procedures.

More particularly, the present invention is based upon incorporating pre-prepared discrete crosslinked polmeric hydrogel bodies at their smallest dehydrated solid dry state shaped in various physical configurations, into the shell before sealing. Later on, as it is required to expand to a desired volume, water is injected into the shell either by device manufacturer or in the operating room before or after the implant is surgically positioned in the patient. The injected water swells and enlarges the small dehydrated hydrogel solid configurations into a larger and softer configurations. After the hydration reaches to a dynamic equilibrium, the prosthesis resembles like a one very large soft hollow ball (shell) packed inside with small and soft macro unit or units (hydrogel filler). This three dimensional arrangement of soft hydrogel units capable of assuming different packing arrangement, can provide the softness with shape memory expected from the filler material as breast implant mechanically moves or depressed while in patient.

Further, more particularly, according to the invention, a well-defined mechanically stable 3-dimensional coated/ uncoated crosslinked almost spherical rigid polymeric units or uncrosslinked almost spherical macro unit or units coated with crosslinked protective coating, at their smallest dehydrated free flowing solid dry state, are placed into inconsiderable volume of a completely deflated shell through a sealable hole and subsequently are expanded to a larger sizes by hydration into a non-bleeding well defined mechanically stable 3-dimensional soft non-soluble water swollen polymeric macro unit or units with no free water in between the enlarged units.

Preferably, according to the invention, a well-defined mechanically stable 3-dimensional cross-linked almost spherical rigid polymeric beads or balls at their smallest dehydrated free flowing solid dry state, are placed into a shell through a sealable hole and subsequently are expanded to a larger sizes by hydration into a non-bleeding well-defined mechanically stable 3-dimensional cross-linked soft and non-soluble water swollen polymeric bead or balls with no free water in-between the balls or beads where the balls or beads are capable of rolling over one another.

Any of the biocompatable hydrogel units produced from hydrophilic monomers or comonomers of either natural or synthetic origin is a suitable filler material for the purpose of practicing the present invention. Without being limited to those exemplified here, a wide range of hydrogel macro unit or units with different structural characteristics can be used as filler material but all should meet the primary requirements of having a network of hydrophilic pores capable of trapping, retaining all the implant injected water and expanding with water absorption while the enlarged units are biocompatable, water insoluble and non-bleeding.

The solid hydrogel units or superabsorbent polymers used according to the present invention are in general prepared by various synthetic techniques using different polymerization processes such as bulk solution and suspension. Furthermore, hydrogel macro unit or units can also be prepared by molding into small shapes or through grinding of larger molded or casted parts into units of desired shapes and sizes.

The polymeric bodies or units can be shaped in various physical forms of irregular granules, spherical, irregular clusters, rod, elliptical, elongated, fiber flock, wrinkled and etc. where new synthetic techniques and modified shapes continue to be developed for improved swelling capacity and hydrated elastic gel modules. Fredric L. Buchholz, Chemtech, September 1994, discloses more information. Thus, the solid filler material in the present invention can be in any size or shapes, mentioned above, as well as mixtures thereof.

A particularly preferred three dimentional physical configuration is spherical, where hydrogel units are shaped as bails, beads or bodies with curved outer surfaces and no sharp edges.

The solid polymeric bodies or units may be further surface crosslinked or coated to improve the performance or to enhance a specific function such as rate of water absorption or to render mechanical stability and water insolubility to a uncrosslinked hydrogel unit. However, the swelling, elasticity, solubility, mechanical and chemical stability of hydrated hydrogel units depend on the precise structure of the polymer network and primarily on the crosslinking density and pore size within the unit or on the surface of the unit.

Generally, any of the natural or synthetic biocompatible polymers capable of forming discrete macro unit or units are suitable for purpose of practicing the present invention. Additionally, by controlling the chemical structure, hydrogel units can be designed to be biodegradable by a mechanism such as enzymatic hydrolysis or just is readily clearable from the body, via the urinary pathway, if the breast implant were to break by the accidental rupture of implant membrane shell as a result of some type of physical or traumatic injury.

Hydrogel polymers, for practicing the present invention, are crosslinked non-sticky solids with no sharp edges in the dehydrated state but swell quickly to become elastic larger units upon water penetration. Swollen hydrogels with no free water in between hydrogel units resemble in many physical properties to biological tissues, and because of their importance in the field of biomaterial, hydrogels and processes for their formation are well documented in the literature. Typical hydrogel materials include crosslinked homopolymers or copolymers of hydroxyalkylmethacrylate or acrylate, hydroxyalkoxymethacrylate or acrylate, polyhydroxyalkylmethacrylate or acrylate or acrylate terminated polyethylene oxide, starch or polyvinyl alcohol grafted sodium polyacrylate, polyacrylamide, polyamino acids, polyvinylpyrrolidone, and natural polymers such as crosslinked protein, starches, or cellulosic derivatives, collagen, polypeptide and polysaccharide hydrogels. Examples of typical crosslinking agents include N,N-methylenebisacryl amide, ethyleneglycoldiacrylate, trimethylolpropanetriacrylate, bisacrylamido acetic acid, methacrylate analogs of the aforementioned acrylates, triallylamine and other di or polyfunctional crosslinkers such as carboxylic acids, amines, isocyanates, alcohols and the like.

Thus we have described a new type of implantable breast prosthesis which prevents bleeding. This is accomplished by a new filler material made out of discrete biocompatible crosslinked hydrogel bodies or units in various possible shapes, where preferably, the hydrogel units are cross-liked polymeric beads or balls, mechanically stable, non-soluble and have a network of hydrophilic pores capable of trapping, retaining all the injected water and expanding with water absorption. Further more, the high affinity of trapped water for hydrophilic pores and large size of water swollen crosslinked units preferably bead or ball will eliminate bleeding/leakage/loss of either water or polymeric unit from hydrophobic breast implant shell.

The following examples are presented to illustrate the practice of the invention and not as an indication of the limits of the scope thereof, the procedures to synthesize and to prepare the suitable polymeric hydrogel units for the practice of this invention are well known in the art of polymer, biomaterial and pharmaceutical fields.

EXAMPLE 1

The breast tissue expander of the present invention is made by first making a shell. Elastomeric shell is made by the usual multiple dipping technique employed by the manufacturer and that includes dipping a mandrel which is shaped to the desired form into film forming solutions or dispersions to make a multiple layered shell where layers can be either the same or different in chemical composition. To produce inter-locked multi-layered shell, it is desirable to cure all different layers by heat or radiation to desired post-cure thickness of less than 0.2mm where the shell is expected to be soft, flexible and elastic.

After the multilayered shell is cured completely, it is removed from the mandrel by stretching the hole at the mandrel attachment site. Subsequently, polymeric hydrogel units at their smaller dehydrated state are placed inside the shell through the large hole to occupy partial space completely on inside periphery. The hole is then sealed by cementing a patch overlapping the periphery of the hole. Subsequently, sterile water is injected with the aid of a filling tube or syringe through a fill patch into the shell either prior to or following implantation.

EXAMPLE 2

Hydrogel beads ranging from below 3500 Angstrom or above like 10 to 850 Micrometer or still larger in diameter are usually produced by suspension polymerization technique. Mono or polydispersed hydrogel beads with various degree of swelling behavior are produced commercially using phase separation polymerization in aqueous solution. The mixture of reacting comonomers include hydrophilic composition such as but not limited to glycol monoester of acrylic or methacrylic acid, acrylamide, vinyl pyrrolidone, hydroxyethyl methacrylate grafted polyethyleneoxide, methacrylated polyvinylalcohol and cross-linking agent like polyoldimethacrylate or diacrylat, polyethyeneglycol diacrylate or dimethacrylate and the like.

A typical process to produce hydrogel beads involves addition of monomer phase comprising cross-linker, initiator and monomer into water in a batch reactor. The monomer phase suspension in water is stabilized by a suspending agent. The polymerization is carried out at 80–90 C. for several hours. After the polymerization is complete, the suspending agent is removed and the hydrogel beads are obtained by filtration. The beads are further purified by soxhlet extraction before being dried and sieved. U.S. Pat. No. 4,138,383 and Kim C., J., Lee, P. I. J. Control. Rel. 1991,16,229 disclose more information.

Obviously many other modification and variations of the composition of this novel polymeric filler material are possible in the light of the teachings given hereinabove. It is, therefore, to be understood, all such variations, modifications, and embodiments are to be regarded as being within the spirit and scope of the invention, as set forth by in the following claims.

I claim:

1. A non-bleeding surgically implantable prosthesis to reconstruct and augment natural breast tissue in human being comprising an outer flexible envelope forming a sealed shell container, where the volume within the container is occupied with a filler material made of discrete biocompatible mechanically stable water swollen soft enlarged crosslinked 3-dimensional hydrated polymeric hydrogel units having a network of pores within the units and with no free water in-between the hydrated units.

2. The prosthesis of claim 1 wherein said polymeric hydrogel units are shapes selected from the group consisting essentially of spherical, irregular granules or clusters, rod, elliptical, elongated, fiber flock, wrinkled and mixtures thereof.

3. The prosthesis of claim 1 wherein said hydrated polymeric hydrogel units are shaped in curved outer surfaces with no sharp edges.

4. The prosthesis of claim 1 wherein said hydrated polymeric hydrogel unit is in shape of bead.

5. The prosthesis of claim 1 wherein said hydrated polymeric hydrogel unit is in shape of ball.

6. The prosthesis of claim 1 wherein each polymeric unit is either natural or synthetic origin, crosslinked and insoluble in water or saline.

7. The prosthesis of claim 1 wherein said hydrated polymeric hydrogel unit is biostable and non-resorbable.

8. The prosthesis of claim 1 wherein said hydrated polymeric hydrogel units are unimodal in shape and size distribution.

9. The prosthesis of claim 1 wherein said hydrated polymeric hydrogel units are unimodal in shape and multimodal in size distribution.

10. The prosthesis of claim 1 wherein said hydrated polymeric hydrogel units are multimodal in shape and size distribution.

11. The prosthesis of claim 1 wherein all the water present in the implant is trapped and retained inside network of pores within discrete polymeric hydrogel units.

12. A method of preparing a surgically implantable prosthesis to reconstruct and augment natural breast tissue in humans, comprising the steps of, placing, discrete mechanically stable 3-dimensional crosslinked polymeric hydrogel units at their smallest dehydrated free flowing solid and dry state into inconsiderable volume of a deflated shell through a sealable hole and subsequently, before or after surgically implanting, water or saline is injected to expand the polymeric hydrogel unit to a larger hydrated size by hydration into discrete mechanically stable 3-dimensional crosslinked soft enlarged and insoluble water swollen polymeric units forming a non-bleeding filler material with no free water in-between the hydrated units.

\* \* \* \* \*